United States Patent [19]

Nichol, Jr. et al.

[11] 3,932,617

[45] Jan. 13, 1976

[54] INTERFERON INDUCTION

[75] Inventors: Francis Richard Nichol, Jr., Newport Beach, Calif.; Gerald E. Underwood, Kalamazoo County, Mich.

[73] Assignee: The Upjohn Company, Kalamazoo, Mich.

[22] Filed: May 24, 1974

[21] Appl. No.: 473,012

[52] U.S. Cl. .................................. 424/85; 424/251
[51] Int. Cl.² ...................................... A61K 31/505
[58] Field of Search ............................ 424/85, 251

[56] References Cited
FOREIGN PATENTS OR APPLICATIONS
1,223,686  3/1971  United Kingdom .................. 424/251

OTHER PUBLICATIONS
Hannig et al., *Pharmazie*, Vol. 23, pp. 614–618, 1968.

*Primary Examiner*—Richard L. Huff
*Attorney, Agent, or Firm*—William G. Jameson; Roman Saliwanchik

[57] ABSTRACT

A method and therapeutic compositions for inducing interferon formation in vivo. To a host is administered an interferon inducer of the formula:

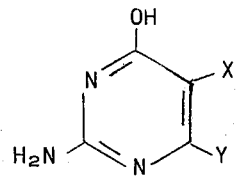

wherein X is a member selected from the group consisting of bromo and iodo and Y is a member selected from the group consisting of methyl and ethyl when X is bromo; or Y is a member selected from the group consisting of methyl, ethyl, n-propyl, benzyl and chloro when X is iodo.

12 Claims, No Drawings

INTERFERON INDUCTION

BACKGROUND OF THE INVENTION

Interferon is the name given to certain protein molecules which appear in the blood or organs of animals, or in the medium of tissue cultures when such are exposed to an interferon inducer. Interferons are helpful in preventing or mitigating viral diseases. In seeking effective ways to induce interferon formation, numerous investigations have been directed to agents and methods to induce interferon formation. Such agents, which lead to the appearance of interferon in the blood or organs of animals, or in the medium of tissue cultures are designated as interferon inducers.

During the past decade a large number of agents have been tested as interferon inducers. Numerous interferon inducers have been reported including various live or killed viruses, endotoxin, phytohaemagglutinin (PHA), bacteria, trachoma, mycoplasmas, protozoa, rickettsiae, nucleic acids, synthetic polymers, mitogens, polysaccharides, antibiotics and tilorone hydrochloride, see Finter, *Interferons and Interferon Inducers* (1973).

BRIEF SUMMARY OF THE INVENTION

This invention relates to new therapeutic compositions and to methods for using same for inducing interferon formation. According to the present invention, an active ingredient is administered to humans or interferon producing animals at doses effective for inducing interferon formation. The active ingredients of this invention consist of compounds having the formula:

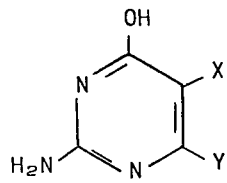

wherein X is a member selected from the group consisting of bromo and iodo and Y is a member selected from the group consisting of methyl and ethyl when X is bromo; or Y is a member selected from the group consisting of methyl ethyl, n-propyl, benzyl and chloro when X is iodo; or the pharmacologically acceptable acid addition salts thereof.

DETAILED DESCRIPTION OF THE INVENTION

This invention relates to new pharmaceutical compositions and a method for inducing interferon formation in vivo. More particularly, this invention relates to pharmaceutical compositions having interferon inducing properties and the method of using said compositions.

The present invention comprises the compositions and the method of inducing interferon formation by administration of a compound selected from the group consisting of compounds having the formula

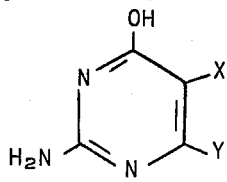

wherein X is a member selected from the group consisting of bromo and iodo and Y is a member selected from the group consisting of methyl and ethyl when X is bromo; or Y is a member selected from the group consisting of methyl, ethyl, n-propyl, benzyl and chloro when X is iodo; or the pharmacologically acceptable acid addition salts thereof; in association with a pharmaceutical carrier.

Suitable pharmacologically acceptable acid addition salts include the hydrochloride, sulfate, phosphate, nitrate, citrate, acetate, lactate, succinate and the like. These salts can be used in the same manner as the base compounds.

According to the present invention, the induction of interferon formation in vivo is achieved by administering the compounds of this invention as described above, hereinafter referred to as active ingredients, to a suitable host. By 'host' is meant interferon producing animals, i.e., intact viable animals which are capable of interferon production. The host may be warm-blooded animals such as mammals, e.g., mice, rats, rabbits, bovine, pigs, hamsters, dogs, cats; guinea pigs, horses, goats, sheep, monkeys, man; and birds, e.g., chickens, ducks, turkeys, pigeons, parakeets, and canaries. The mode of administration can be parenterally such as subcutaneously, intramuscularly, intradermally, intraperitoneally, intravenously or locally, preferably on a mucous membrane such as intranasally, pharyngolaryngeally, bronchially, broncholially, intravaginally, rectally or ocularly. The mode of administration can also be by implantation. Alternatively or concurrently, administration can be by the oral route, a preferred mode of administration for an interferon inducer. Practically, it is advantageous to administer the active ingredient to the host orally, intranasally, subcutaneously or intramuscularly.

The induction of interferon by administration of an active ingredient is demonstrated by established interferon assay methods such as plaque-reduction, see Finter, *Interferons and Interferon Inducers*, (1973). The interferon induced by the administration of an active ingredient can also be demonstrated by the protection of the host animals as well as tissue cultures against virus challenge.

The induction of interferon formation by the administration of an active ingredient of this invention has been demonstrated using established interferon plaquereduction assay procedures as described above. For example, the induction of interferon formation by the administration of 2-amino-5-bromo-6-methyl-4-pyrimidinol has been demonstrated in mice and rats using said established interferon plaque-reduction assay procedures. However, in limited testing, 2-amino-5-bromo-6-methyl-4-pyrimidinol has not induced measurable interferon levels in rabbits, dogs and monkeys with the route and at the dose levels administered. Nevertheless, it is anticipated that when FDA approval is obtained to test the active ingredients in man, that the results in man will follow the positive results shown in mice. Further, it is anticipated that proper dosage regimens of 2-amino-5-bromo-6-methyl-4-pyrimidinol in other warm-blooded animals will yield positive interferon induction results.

The dosage administered will be dependent upon the level of interferon desired, the type of animal involved, its age, health, weight, kind of concurrent treatment, if any, and frequency of treatment. Illustratively, dosage levels of the administered active ingredients can be: intravenous, 0.1 to about 50 mg./kg.; intraperitoneal, 0.1 to about 250 mg./kg.; subcutaneous, 0.1 to about 250 mg./kg.; intramuscular, 0.1 to about 250 mg./kg.; orally, 0.5 to about 500 mg./kg., and preferably about 5 to 250 mg./kg.; intranasal instillation, 0.1 to about 50 mg./kg.; and aerosol, 0.1 to about 50 mg./kg. of animal (body) weight.

Expressed in terms of concentration, an active ingredient can be present in the compositions of the present invention for localized use about the cutis, intranasally, pharyngolaryngeally, bronchially, broncholially, intravaginally, rectally, or ocularly in a concentration of from about 0.1 to about 25% w/w of the composition; preferably about 1 to about 5% w/w of the composition; and for parenteral use in a concentration of from about 0.5 to about 50% w/v of the composition and preferably from about 1 to about 10% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methyl-cellulose and a polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampul and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal route can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred.

The active ingredients can also be admixed in animal feed. The active ingredients can conveniently be prepared in the form of a food premix. The food premix can comprise an active ingredient in admixture with an edible pharmaceutical diluent such as starch, oatmeal, flour, calcium carbonate, talc, dried fish meal and the like non-toxic, orally acceptable pharmaceutical diluents. The prepared premix is then conveniently added to the regular feed.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as co-solvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampuls, vials, segregated multiples of any of the foregoing, and other forms as herein described.

The active ingredients to be employed as interferon inducers can be easily prepared with the employment of raw materials which themselves are available in the art and can be made by established procedures. The following preparations are illustrative of the preparation of the active ingredients of the present invention, but are not intended to be limiting.

PREPARATION 1

2-Amino-5-bromo-6-methyl-4-pyrimidinol can be prepared according to the method of Hull et al., J. Chem. Soc. 41, 46 (1947) and the method of Nishiwaki et al., Bull Chem. Soc. Jap. 33, 26 (1960).

PREPARATION 2

2-Amino-5-bromo-6-ethyl-4-pyrimidinol

A. By bromination of 6-ethyl-isocytosine with N-bromosuccinimide

To a faintly warm solution of 1.112 g. (8.0 millimoles) of 6-ethyl-isocytosine in 16 ml. of glacial acetic acid is added 1.424 g. (8.0 millimoles) of N-bromosuccinimide. The reaction flask is closed with a drying tube, and the mixture heated briefly on a steam bath, with occational swirling, until solution is complete. The solution is heated on a steam bath for one hour, then allowed to cool spontaneously. The cooled solution is seeded with crystals from an earlier run and kept at ambient temperature for several days. The resulting crystals are collected, washed first with cool glacial acetic acid then with anhydrous ether. The material is dried, first in air then in vacuo at 76°C. for several hours. The crude material 960 mg. is crystallized from about 20 ml. of 50% aqueous acetic acid, using decolorizing charcoal. The product is collected, washed successively with cold 50% aqueous acetic acid, cold 95% ethanol and anhydrous ether. The pure material, after brief air-drying, is dried in vacuo at ca. 80°C. There is thus obtained 660 mg. of 2-amino-5-bromo-6-ethyl-4-pyrimidinol which melts at 225° to 225.5° centigrade, has $\lambda max^{0.1N\ NaOH}$ 230.5 nm. ($\epsilon 8,200$); 283 nm. ($\epsilon 7,200$) and the infrared absorption below.

NH/OH, 3380, 3320, 3130, 2720; C=O/C=N/C=C, 1675, 1640, 1610, 1565; C—O/C—N other, 1340, 1310, 1215, 1060, 1005 cm$^{-1}$.

Analysis Calcd. for: $C_6H_8BrN_3O$: C, 33.05; H, 3.71; Br, 36.65; N, 19.27. Found: C, 32.98; H, 3.63; Br, 36.75; N, 18.81.

B. By bromination of 6-ethyl-isocytosine with bromine in acetic acid

With magnetic stirring, a mixture of 6.0 g. (43.2 millimoles) of 6-ethyl-isocytosine in 50 ml. of glacial acetic acid is warmed slightly to effect solution. To the warm, stirred solution is added 2.25 ml. (6.6 g.; 41.3 millimoles) of bromine. An exothermic reaction occurs immediately and a yellow solid precipitates. The reaction mixture is allowed to cool to room temperature spontaneously. After three hours, the yellow solid is collected and washed, first with glacial acetic acid, then with anhydrous ether and dried in air. The crude solid is dissolved in 150 ml. of boiling water. The resulting colorless solution is allowed to cool to ca. 25°C. spontaneously, then stored at 5°C. overnight. The crystalline material is collected, washed thoroughly with water, then cold 95% ethanol and finally with dry ether. Yield of first crop material, 3.86 g. The combined filtrate from this material is evaporated to a volume of about 25 ml. in vacuo. The resulting solid is collected, washed with acetone and dried. Yield, of second-crop material, 1.80 g. The filtrate from the second crop material is concentrated to a volume of approximately 25 ml. and the concentrate neutralized with concentrated ammonium hydroxide. The resulting precipitate is collected, washed with water, then with acetone and dried to afford 2.0 g. of third crop material. The three crops of solid are shown by thin layer chromatography to be identical. Crystallization of the combined crops [7.66 g. (85.2%)] from 150 ml. of 50% aqueous acetic acid gives 6.23 g. (81.3% recovery) of 2-amino-5-bromo-6-ethyl-4-pyrimidinol.

PREPARATION 3

2-Amino-5-iodo-6-methyl-4-pyrimidinol

With protection from external moisture throughout, 250.3 mg. (2.0 millimoles) of finely powdered 6-methyl-isocytosine is dissolved in 4 ml. of hot glacial acetic acid. While still hot, 450 mg. (2.0 millimoles) of N-iodosuccinimide is added to the solution and the whole is heated on a steam bath for five minutes with occasional swirling. The reaction mixture is removed from the steam bath and allowed to stand at ambient temperature. After three and one-half hours, water is added, the crystalline cake is crushed, the solid collected, washed with water, then acetone and dried in air. The crude material [335 mg.] is crystallized from approximately 10 ml. of glacial acetic acid. After being kept at room temperature overnight, the pure compound is collected, washed with its mother liquor, then with anhydrous ether repeatedly and dried in vacuo at ca. 90°C. There is thus obtained 220 mg. of 2-amino-5-iodo-6-methyl-4-pyrimidinol which melts at 211.5° to 212.5°C. with previous darkening and sintering, has $\lambda max^{0.1N\ NaOH}$ 236 nm. ($\epsilon 9,900$); 284 nm. ($\epsilon 10,900$) and the infrared absorption below.

NH/OH, 3480, 3380, 3300, 3120; C=O/C=C/C=$\lambda$ N/Other, 1675$_{sh}$, 1645$_{sh}$, 1630$_{sh}$, 1590, 1560$_{sh}$; C—O/C-N/Other, 830, 765, 675 cm$^{-1}$.

Analysis Calcd. for: $C_5H_6IN_3O$: C, 23.92; H, 2.41; 1,50.55; N, 16.74. Found: C, 24.22; H, 2.38; 1,50.67; N, 15.86.

PREPARATION 4

2-Amino-5-iodo-6-ethyl-4-pyrimidinol

To a slightly warm solution of 556 mg. (4.0 millimoles) of 6-ethyl-isocytosine in 8 ml. of glacial acetic acid is added 900 mg. (4.0 millimoles) of N-iodosuccinimide. The reaction flask is fitted with a drying tube, the mixture heated on a steam bath for three minutes with intermittent swirling to complete solution, and heating is continued for an additional 65 minutes. The solution is allowed to cool spontaneously, whereupon crystallization begins within less than thirty minutes. The mixture is kept at about 25°C. for 72 hours. The pale yellow crystals are collected, washed with cool glacial acetic acid followed by anhydrous ether. The material is dried in air for a short time, then in vacuo at 76°C. Yield, 770 mg. Crystallization of the crude material from ca. 50 ml. of 95% ethanol, using decolorizing charcoal affords 540 mg. of 2-amino-5-iodo-6-ethyl-4-pyrimidinol which melts at 199° to 200°C., has $\lambda max^{0.1N}_{NaOH}$ 236 nm. ($\epsilon 9,950$); 285 nm. ($\epsilon 6,950$) and the infrared absorption below.

NH/OH, 3440, 3400, 3340, 3200, 3080, ~2950; C=O/C=C/C=N/NH deformation, 1640, 1605, 1560, 1515; C—N/C—O/Other, 1305, 1215, 1136, 1000, 775 cm$^{-1}$.

Analysis Calcd. for: $C_6H_8IN_3O$: C, 27.19; H, 3.04; I, 47.88; N, 15.86. Found: C, 27.16; H, 3.01; I, 47.48; N, 15.89.

PREPARATION 5

2-Amino-5-iodo-6-n-propyl-4-pyrimidinol

A suspension of 149.1 mg. (0.973 millimole) of 6-n-propyl-isocytosine in 3 ml. of dimethylformamide (DMF) is warmed slightly and the resulting solution cooled to ca. 25°C. To the cooled solution is added 226.6 mg. (1.008 millimoles) of N-iodosuccinimide, and the mixture is swirled until solution is complete. The reaction mixture is kept at ambient temperature, with exclusion of external moisture for ca. 18 hours. The precipitated crystals are collected, washed well with acetone and air-dried. Yield, 75 mg. The combined filtrate is evaporated in vacuo and the residual yelloworange solid is azeotroped under reduced pressure twice with absolute ethanol. The dry residual solid is triturated thoroughly with acetone, the insoluble fraction collected, washed with acetone and dried in air. Yield, of second crop material, 144 mg. The combined crops are dissolved in about 12 ml. of hot absolute ethanol, the solution concentrated to a volume of ca. 4 ml. and kept at room temperature overnight. The crystals are collected, washed with absolute ethanol and dried. Recrystallization of this material (122 mg.) from absolute ethanol affords 92 mg. of 2-amino-5-iodo-6-n-propyl-4-pyrimidinol which melts at 233° to 234°C. with previous darkening, has $\epsilon max^{0.1N\ NaOH}$ 236 nm. ($\epsilon 10,000$); 286 nm. ($\epsilon 6,850$) and the infrared absorption below.

NH/OH, 3450, 3390, 3340, 3200,~2850; C=O/C=C/C=N/Other, 1640, 1600, 1560, 1545, 1520; C—O/C—N/Other, 1210, 1140, 1000, 900 cm$^{-1}$.

Analysis Calcd. for: $C_7H_{10}IN_3O$: C, 30.12; H, 3.61; N, 15.06* Found: C, 30.30; H, 3.34; N, 14.99

*The iodine value found for this compound was higher than acceptable limits

PREPARATION 6

2-Amino-5-iodo-6-benzyl-4-pyrimidinol

Six milliliters of dimethylformamide (DMF) are added to 394.4 mg. (1.965 millimoles) of 6-benzylisocytosine. The suspension is heated until solution is complete. 458.2 mg. (2.04 millimoles) of 4-iodo-succinimide is added, the last traces being rinsed into the reaction mixture with a small volume of DMF. With protection from external moisture, the reaction mixture is allowed to stand at ambient temperature overnight. Addition of 10 ml. of water to the reaction mixture precipitates a solid. The latter is collected, washed with water followed by acetone, then anhydrous ether and airdried. The crude material [465.7 mg. (72.3%); m.p. ca. 217°C. (dec.)] is dissolved in hot DMF, the solution filtered and the filtrate diluted slowly with water to distinct turbidity. Crystallization starts immediately when the solution begins to cool. The mixture is kept at room temperature for about two hours. The crystals are collected, washed successively with water, absolute ethanol, and anhydrous ether and dried in vacuo at ca. 25°C. overnight. There is thus obtained 432 mg. of 2-amino-5-iodo-6 -benzyl-4-pyrimidinol which melts at 216° to 217°C. with previous softening and darkening, has $\lambda max^{0.1N\ NaOh}$ 238 nm. ($\epsilon$ 10,850); 269 n.m. sl.sh. ($\epsilon$ 4,400); 278 n.m. sl. sh. ($\epsilon$ 5,950); 289 n.m. ($\epsilon$ 7,000) and the infrared absorption below.

NH/OH, $3440_{w.}$, 3340, 3140, 2730; C=O/C=N/C=C/NH, 1635, 1660, 1560, 1495; C—N/C—O/other, 1350, 1335, 1220, 1190, 1015; Mono CH/other; 775, 745, 695 cm$^{-1}$.

Analysis Calcd. for: $C_{11}H_{10}IN_3O$. C, 40.40; H, 3.08; I, 38.81; N, 12.85. Found: C, 40.43; H, 2.98; I, 38.84; N, 12.43.

PREPARATION 7

2-Amino-5-iodo-6-chloro-4-pyrimidinol

To 1.45 grams (10.0 millimoles) of 6-chloro-isocytosine is added 15 ml. of dimethylformamide (DMF) and 2.27 grams (10.08 millimoles) of N-iodosuccinimide. With protection from external moisture, the mixture is heated on a steam bath for one-hour hour. The resulting brownish red solution is allowed to stand overnight at room temperature with continued exclusion of moisture. The solution is evaporated under reduced pressure and the residual solid azeotroped once with ethanol in vacuo. The resulting solid is triturated with glacial acetic acid. The insoluble solid is collected, washed with a small volume of glacial acetic acid, then with acetone. The solid is re-triturated with glacial acetic acid, collected, washed with acetone and air-dried. Yield, 1.50 g. Evaporation of the combined filtrate in vacuo, trituration of the residue with water, then acetone gives, after collecting and drying, 970 mg. of second-crop material. The first-crop material is crystallized twice from glacial acetic acid to give 540 mg. of 2-amino-5-iodo-6-chloro-4-pyrimidinol which decomposes at >270°, has $\lambda max^{0.1N\ NaOh}$ 236 nm. ($\epsilon 9,150$); 285 nm. ($\epsilon 6,200$) and the infrared absorption below.

NH/CH, 3380, 3300, 3190, 3130; O=O/C=C/C=N/NH deformation, $1670_{v.s.}$, 1580, 1540; C—N/Other, 1320, 1215, 1010; Other, 910, 755 cm$^{-1}$.

Analysis Calcd. for: $C_4H_3ClIN_3O$: C, 17.73; H, 1.11; Cl, 13.08; I, 46.83; N, 15.51. Found: C, 18.51; H, 2.24; Cl, 13.38; I, 46.50; N, 14.70.

The following examples are illustrative of the best mode contemplated by the inventors for carrying out their invention and are not to be construed as limiting.

EXAMPLE 1

Hard-Gelatin Capsules

One thousand two-piece hard gelatin capsules for oral use, each capsule containing 100 mg. of 2-amino-5-bromo-6-methyl-4-pyrimidinol, are prepared from the following types and amounts of ingredients:

| | |
|---|---|
| 2-Amino-5-bromo-6-methyl-4-pyrimidinol, micronized | 100 Gm. |
| Lactose | 100 Gm. |
| Corn starch | 20 Gm. |
| Talc | 20 Gm. |
| Magnesium stearate | 2 Gm. |

The 2-amino-5-bromo-6-methyl-4-pyrimidinol, finely divided by means of an air micronizer, is added to the other finely powdered ingredients, mixed thoroughly and then encapsulated in the usual manner.

The foregoing capsules are useful for inducing interferon formation by the oral administration of one or two capsules one to four times a day.

Using the procedure above, capsules are similarly prepared containing 2-amino-5-bromo-6-methyl-4-pyrimidinol in 50, 250 and 500 mg. amounts by substituting 50 Gm., 250 Gm. and 500 Gm. of 2-amino-5-bromo-6-methyl-4-pyrimidinol for the 100 Gm. used above.

EXAMPLE 2

Soft Gelatin Capsules

One-piece soft gelatin capsules for oral use, each containing 250 mg. of 2-amino-5-bromo-6-methyl-4-pyrimidinol (finely divided by means of an air micronizer), are prepared by first suspending the compound in 0.5 ml. of corn oil to render the material capsulatable and then capsulating in the above manner.

The foregoing capsules are useful for inducing interferon formation by the oral administration of one or two capsules one to four times a day.

EXAMPLE 3

Tablets

One thousand tablets, each containing 500 mg. of 2-amino-5-bromo-6-methyl-4-pyrimidinol, are prepared from the following types and amounts of ingredients:

| | |
|---|---|
| 2-Amino-5-bromo-6-methyl-4-pyrimidinol | 500 Gm. |
| Lactose | 75 Gm. |
| Corn starch | 50 Gm. |
| Magnesium stearate | 4 Gm. |
| Light liquid petrolatum | 5 Gm. |

The 2-amino-5-bromo-6-methyl-4-pyrimidinol, finely divided by means of an air micronizer, is added to the other ingredients and then thoroughly mixed and slugged. The slugs are broken down by forcing through a Number Sixteen screen. The resulting granules are then compressed into tablets, each tablet containing 500 mg. of 2-amino-5-bromo-6-methyl-4-pyrimidinol.

The foregoing tablets are useful for inducing interferon formation by the oral administration of one or two tablets one to four times a day.

Using the procedure above, tablets are similarly prepared containing 2-amino-5-bromo-6-methyl-4-pyrimidinol in 250 mg. and 100 mg. amounts by substituting 250 Gm. and 100 Gm. of 2-amino-5-bromo-6-methyl-4-pyrimidinol for the 500 Gm. used above.

EXAMPLE 4

Oral Suspension

One thousand ml. of an aqueous suspension for oral use, containing in each teaspoonful (5 ml.) dose, 500 mg. of 2-amino-5-bromo-6-methyl-4-pyrimidinol, is prepared from the following types and amounts of ingredients:

| | |
|---|---|
| 2-Amino-5-bromo-6-methyl-4-pyrimidinol, micronized | 100 Gm. |
| Citric acid | 2 Gm. |
| Benzoic acid | 1 Gm. |
| Sucrose | 700 Gm. |
| Tragacanth | 5 Gm. |
| Lemon oil | 2 Gm. |
| Deionized water, q.s. 1000 ml. | |

The citric acid, benzoic acid, sucrose, tragacanth and lemon oil are dispersed in sufficient water to make 850 ml. of solution. The 2-amino-5-bromo-6-methyl-4-pyrimidinol, finely divided by means of an air micronizer, is stirred into the syrup until uniformly distributed. Sufficient water is added to make 1000 ml.

The composition so prepared is useful for inducing interferon formation at a dose of 1 tablespoonful (15 ml.) three times a day.

EXAMPLE 5

A sterile aqueous suspension for parenteral injection, containing in 1 ml. 300 mg. of 2-amino-5-bromo-6-methyl-4-pyrimidinol, is prepared from the following types and amounts of ingredients:

| | | |
|---|---|---|
| 2-Amino-5-bromo-6-methyl-4-pyrimidinol, micronized | 300 | Gm. |
| Polysorbate 80 | 5 | Gm. |
| Methylparaben | 2.5 | Gm. |
| Propylparaben | 0.17 | Gm. |
| Water for injection, q.s. 1000 ml. | | |

All the ingredients, except the 2-amino-5-bromo-6-methyl-4-pyrimidinol, are dissolved in the water and the solution sterilized by filtration. To the sterile solution is added the sterilized 2-amino-5-bromo-6-methyl-4-pyrimidinol, finely divided by means of an air micronizer, and the final suspension is filled into sterile vials and the vials sealed.

EXAMPLE 6

Suppository, Rectal

One thousand suppositories, each weighing 2.5 Gm. and containing 150 mg. of 2-amino-5-bromo-6-methyl-4-pyrimidinol are prepared from the following types and amounts of ingredients:

| | | |
|---|---|---|
| 2-Amino-5-bromo-6-methyl-4-pyrimidinol, micronized | 150 | Gm. |
| Polysorbate 80 | 5 | Gm. |
| Methylparaben | 2.5 | Gm. |
| Propylparaben | 0.17 | Gm. |
| Deionized water, q.s. 1000 ml. | | |

The 2-amino-5-bromo-6-methyl-4-pyrimidinol is finely divided by means of an air micronizer and added to the propylene glycol and the mixture passed through a colloid mill until uniformly dispersed. The polyethylene glycol 4000 is melted and the propylene glycol dispersion added slowly with stirring. The suspension is poured into unchilled molds at 40°C. The composition is allowed to cool and solidify and then removed from the mold and each suppository foil wrapped.

The foregoing suppositories are inserted rectally for inducing interferon formation.

EXAMPLE 7

Intranasal Suspension

One thousand ml. of a sterile aqueous suspension for intranasal instillation, containing in each ml. 150 mg. of 2-amino-5-bromo-6-methyl-4-pyrimidinol, is prepared from the following types and amounts of ingredients:

| | |
|---|---|
| 2-Amino-5-bromo-6-methyl-4-pyrimidonal, micronized | 150 Gm. |
| Propylene glycol | 150 Gm. |
| Polyethylene glycol, 4000 q.s. | 2,500 Gm. |

All the ingredients, except the 2-amino-5-bromo-6-methyl-4-pyrimidinol, are dissolved in the water and the solution sterilized by filtration. To the sterile solution is added the sterilized 2-amino-5-bromo-6-methyl-4-pyrimidinol, finely divided by means of an air micronizer, and the final suspension is aseptically filled into sterile containers.

The composition so prepared is useful for inducing interferon formation by the intranasal instillation of 0.2 to 0.5 ml. given one to four times per day.

EXAMPLE 8

Animal Feed

One thousand grams of feed premix is prepared from the following types and amounts of ingredients:

| | |
|---|---|
| 2-Amino-5-bromo-6-methyl-4-pyrimidinol | 20 Gm. |
| Soybean meal | 400 Gm. |
| Fish meal | 400 Gm. |
| Wheat germ oil | 50 Gm. |
| Sorghum molasses | 130 Gm. |

The ingredients are mixed together and pressed into pellets.

The premix can be fed to laboratory animals directly, i.e., rats and mice, for induction of interferon formation.

For larger animals the premix can be added to the animal's regular feed in an amount calculated to give the desired dose of 2-amino-5-bromo-6-methyl-4-pyrimidinol. For example, one part of premix is added to 2.5 parts of a cat's regular feed to provide the desired dose of 200 mg./kg./day for a cat of 2.5 kg.

An active ingredient can also be present, as shown in Examples 9–12, in the undiluted pure form for use locally about the cutis, intranasally, pharyngolaryngeally, bronchially, bronchially, or orally.

EXAMPLE 9

Powder

Five hundred grams of 2-amino-5-bromo-6-methyl-4-pyrimidinol in bulk form is finely divided by means of an air micronizer. The micronized powder is placed in a shaker-type container.

The foregoing composition is useful for inducing interferon formation at localized sites by applying the powder one to four times per day.

EXAMPLE 10

Oral Powder

One thousand grams of 2-amino-5-bromo-6-methyl-4-pyrimidinol in bulk form is finely divided by means of an air micronizer. The micronized powder is divided into individual doses of 250 mg. and packaged.

The foregoing powders are useful for inducing interferon formation by the oral administration of one or two powders suspended in a glass of water, one to four times per day.

EXAMPLE 11

Insufflation

One thousand grams of 2-amino-5-bromo-6-methyl-4-pyrimidinol in bulk form is finely divided by means of an air micronizer.

The foregoing composition is useful for inducing interferon formation by the inhalation of 30 to 75 mg. one to four times per day.

EXAMPLE 12

Hard Gelatin Capsules

One thousand two-piece hard gelatin capsules for oral use, each capsule containing 100 mg. of 2-amino-5-bromo-6-methyl-4-pyrimidinol, are prepared from 100 grams of 2-amino-5-bromo-6-methyl-4-pyrimidinol.

The 2-amino-5-bromo-6-methyl-4-pyrimidinol is finely divided by means of an air micronizer and encapsulated in the usual manner.

The foregoing capsules are useful for inducing interferon formation by the oral administration of one or two capsules one to four times a day.

Using the procedure above, capsules are similarly prepared containing 2-amino-5-bromo-6-methyl-4-pyrimidinol in 50, 250 and 500 mg. amounts by substituting 50 Gm., 250 Gm. and 500 Gm. of 2-amino-5-bromo-6-methyl-4-pyrimidinol for the 100 Gm. used above.

EXAMPLE 13

Following the procedure of the preceding Examples 1 through 12, inclusive, compositions are prepared substituting equivalent amounts of the pharmaceutically acceptable acid addition salts of 2-amino-5-bromo-6-methyl-4-pyrimidinol for the free base of the examples.

EXAMPLE 14

Following the procedure of the preceding Examples 1 through 12, inclusive, compositions are prepared substituting equivalent amounts of 2-amino-5-bromo-6-ethyl-4-pyrimidinol, 2-amino-5-iodo-6-methyl-4-pyrimidinol, 2-amino-5-iodo-6-ethyl-4-pyrimidinol, 2-amino-5-iodo-6-n-propyl-4-pyrimidinol, 2-amino-5-iodo-6-benzyl-4-pyrimidinol, 2-amino-5-iodo-6-chloro-4-pyrimidinol or the pharmaceutically acceptable acid addition salts of each of the foregoing compounds for 2-amino-5-bromo-6-methyl-4-pyrimidinol of each of the examples to provide similar therapeutic properties.

What is claimed is:

1. A method for inducing interferon formation in humans or interferon producing animals which comprises administering to said human or animal an amount effective to induce interferon formation in said human or animal of a compound selected from the group consisting of compounds having the formula:

wherein X is a member selected from the group consisting of bromo and iodo and Y is a member selected from the group consisting of methyl and ethyl when X is bromo; or Y is a member selected from the group consisting of methyl, ethyl, n-propyl, benzyl and chloro when X is iodo; or the pharmacologically acceptable acid addition salts thereof.

2. A method for inducing interferon formation according to claim 1, wherein the compound is administered to the human or interferon producing animal in unit dosage form, from about 0.1 to about 500 milligrams per kilogram body weight of the human or animal.

3. A method for inducing interferon formation according to claim 2, wherein the compound is 2-amino-5-bromo-6-methyl-4-pyrimidinol or the pharmacologically acceptable acid addition salts thereof.

4. A method for inducing interferon formation according to claim 2, wherein the compound is 2-amino-5-bromo-6-ethyl-4-pyrimidinol or the pharmacologically acceptable acid addition salts thereof.

5. A method for inducing interferon formation according to claim 2, wherein the compound is 2-amino-5-iodo-6-methyl-4-pyrimidinol or the pharmacologically acceptable acid addition salts thereof.

6. A method for inducing interferon formation according to claim 2, wherein the compound is 2-amino-5-iodo-6-ethyl-4-pyrimidinol or the pharmacologically acceptable acid addition salts thereof.

7. A method for inducing interferon formation according to claim 2, wherein the compound is 2-amino-5-iodo-6-n-propyl-4-pyrimidinol or the pharmacologically acceptable acid addition salts thereof.

8. A method for inducing interferon formation according to claim 2, wherein the compound is 2-amino-5-iodo-6-benzyl-4-pyrimidinol or the pharmacologically acceptable acid addition salts thereof.

9. A method for inducing interferon formation according to claim 2, wherein the compound is 2-amino-5-iodo-6-chloro-4-pyrimidinol or the pharmacologically acceptable acid addition salts thereof.

10. A pharmaceutical composition comprising, in unit dosage form, from about 25 to about 5000 milligrams of a member selected from the group consisting of
    2-amino-5-bromo-6-methyl-4-pyrimidinol,
    2-amino-5-bromo-6-ethyl-4-pyrimidinol,
    2-amino-5-iodo-6-methyl-4-pyrimidinol,
    2-amino-5-iodo-6-ethyl-4-pyrimidinol,
    2-amino-5-iodo-6-n-propyl-4-pyrimidinol,
    2-amino-5-iodo-6-benzyl-4-pyrimidinol, and
    2-amino-5-iodo-6-chloro-4-pyrimidinol, or the pharmacologically acceptable acid addition salts thereof as an essential active ingredient,
in association with a sweetened flavored pharmaceutical carrier.

11. A pharmaceutical composition comprising, in unit dosage form, from about 0.5 percent to about 98 percent of a member selected from the group consisting of
    2-amino-5-bromo-6-methyl-4-pyrimidinol,
    2-amino-5-bromo-6-ethyl-4-pyrimidinol,
    2-amino-5-iodo-6-methyl-4-pyrimidinol,
    2-amino-5-iodo-6-ethyl-4-pyrimidinol,
    2-amino-5-iodo-6-n-propyl-4-pyrimidinol,
    2-amino-5-iodo-6-benzyl-4-pyrimidinol, and
    2-amino-5-iodo-6-chloro-4-pyrimidinol, or the pharmacologically acceptable acid addition salts thereof as an essential active ingredient,
in association with a sweetened flavored pharmaceutical carrier.

12. A sterile pharmaceutical composition for parenteral administration comprising from about 0.5 percent to about 50 percent, w/v, of a member selected from the group consisting of
    2-amino-5-bromo-6-methyl-4-pyrimidinol,
    2-amino-5-bromo-6-ethyl-4-pyrimidinol,
    2-amino-5-iodo-6-methyl-4-pyrimidinol,
    2-amino-5-iodo-6-ethyl-4-pyrimidinol,
    2-amino-5-iodo-6-n-propyl-4-pyrimidinol,
    2-amino-5-iodo-6-benzyl-4-pyrimidinol, and
    2-amino-5-iodo-6-chloro-4-pyrimidinol, or the pharmacologically acceptable acid addition salts thereof as an essential active ingredient,
in association with a sterile vehicle.

* * * * *